(12) United States Patent
O'Brien et al.

(10) Patent No.: US 6,952,969 B2
(45) Date of Patent: Oct. 11, 2005

(54) CERAMIC BALL BEARING FRACTURE TEST METHOD

(75) Inventors: Michael James O'Brien, Los Angeles, CA (US); Benjamin Allen Nelson, Los Angeles, CA (US)

(73) Assignee: The Aerospace Corporation, El Segundo, CA (US)

( * ) Notice: Subject to any disclaimer, the term of this patent is extended or adjusted under 35 U.S.C. 154(b) by 188 days.

(21) Appl. No.: 10/675,052

(22) Filed: Sep. 30, 2003

(65) Prior Publication Data

US 2005/0066741 A1 Mar. 31, 2005

(51) Int. Cl.[7] ................................................. G01N 3/08
(52) U.S. Cl. ........................................... 73/818; 73/825
(58) Field of Search ................................. 73/818–825

(56) References Cited

U.S. PATENT DOCUMENTS 4,677,855 A * 7/1987 Coffin et al. .................. 73/799
5,369,675 A * 11/1994 Diaz et al. ................... 376/249

* cited by examiner

*Primary Examiner*—Max Noori
*Assistant Examiner*—Alandra Ellington
(74) *Attorney, Agent, or Firm*—Derrick Michael Reid

(57) ABSTRACT

A mechanical test method prescribes compressing brittle balls in spherical conforming opposing platens producing equatorial bulging, tensile stresses, and resulting indentation crack growth that is imaged for providing direct measurement of the fracture toughness of brittle balls, such as, silicon-nitride balls used in hybrid bearings as well as conventional steel ball bearings, with measurement errors being immune to characterizing the dimensions and positioning of the precrack indentations, so that, the test method is accurate, repeatable, and robust.

16 Claims, 6 Drawing Sheets

FRACTURE TOUGHNESS TEST FIXTURE

FRACTURE TOUGHNESS TEST FIXTURE

INDENTATION CRACK

FRACTURE TOUGHNESS MEASUREMENT PROCESS

COMPRESSIVE STRESS CONTOUR PLOT

TENSILE STRESS CONTOUR PLOT

CRACK LENGTH TO TENSILE STRESS GRAPH

CERAMIC BALL BEARING FRACTURE TEST METHOD

FIELD F THE INVENTION

The invention relates to the field of materials fracture testing. More particularly, the present invention relates to ceramic and metallic ball bearing fracture testing for manufacturing and qualifying high quality brittle ball bearings.

BACKGROUND OF THE INVENTION

Over the last decade, silicon-nitride $Si_3N_4$ balls have become an important component of advanced bearings used in a wide range of applications. The greatest commercial success for $Si_3N_4$ balls has been their use in hybrid bearings that combine the ceramic balls with steel races and that are known as silicon-nitride hybrid bearings. Compared to the steel balls, which the silicon-nitride balls replace, the ceramic balls are harder and less dense and offer higher compressive strength, better corrosion resistance, elevated operating temperature, and reduced lubrication requirements. These benefits make the hybrid bearings ideal for severe high-speed applications such as machine tool spindles, high speed dental drills, vacuum turbomolecular pumps, and the liquid-oxygen turbomolecular pumps used in the space shuttle main engines. Large diameter ceramic balls recently became the leading technology for hip replacements. The FDA requires fracture toughness testing of a substituted rectilinear specimen. Hence, a rigorous fracture toughness test that can be used by the FDA and orthopedic manufacturers is desirable for hip ball joints as well.

For exemplar future use in the space industry, the hybrid bearings have been proposed for the improved momentum control wheels and flywheels for satellites. Importantly, the hybrid bearings have recently been used in roller blades, an application where the bearings represent a mass marketing opportunity for lightweight rugged bearings. The roller blade market, as well as other commercial applications, provides recreational users and athletes with cost-effective high technology long-lasting bearings with improved performance in high volumes that would lower the price of the hybrid bearings for all applications with increasing overall sales. For machine tool spindles, the market for hybrid bearings was at $35 million in 2000 and is projected to reach $150 million by 2005, and hence there is wide spread usage. The overall sales of hybrid bearing should reach several hundred million by 2010. Hence, there is a significant need for high-volume hybrid bearings subject to repeatable and accurate manufacturing requirements.

Ceramic balls have significant drawbacks and limitations. Like all ceramics, the silicon-nitride balls have a low tensile strength, which is a fundamental material property. Therefore, under applied tension, the balls are prone to crack either at a preexisting manufacturing flaw or at a flaw that develops during service and usage. A closely related fundamental material property is the fracture toughness, which indicates the susceptibility to fracture of the ceramic material. Low fracture toughness is most important factor indicating the ruggedness and usefulness of all ceramics in general as well as the silicon-nitride balls, in particular. Fortunately, highly engineered ceramics have been developed whose fracture toughness can be significantly increased through processing that controls microstructures. Precise manufacturing can control the size and number of preexisting flaws. To produce tougher ceramics is therefore a two-fold task. First, a microstructure is selected that is intrinsically tougher, which reduces the severity of any flaws. Second, the preexisting flaws are eliminated, which ameliorates the low fracture toughness.

In the specific case of silicon-nitride balls, manufacturing processing has been developed that provides, for example, a two-phase microstructure of alpha and beta silicon nitride where the minor second phase is a blocky shape in a matrix of the major phase. As a micromechanism, this microstructure promotes crack deflection and blunting, which raises the intrinsic fracture toughness. In addition, the ceramic balls are manufactured from a starting powder through hot-isostatic pressing that is followed by grinding and lapping to provide precise spherical shapes. Accurate control of the hot-isostatic pressing eliminates sintering voids and inclusions that are potential preexisting flaws leading to potential fracture and failure of the balls. Precise control of the grinding and lapping eliminates surface cracks. Inspection and nondestructive evaluations are also used to screen balls with preexisting flaws from usage especially in critical applications.

Hence, it is highly desirable to have a manufacturing test that measures the fracture toughness of mass produced silicon-nitride balls. Ideally, the test should be simple and robust enough to b used for quality control by manufacturers and for qualification by contractors installing the balls in critical applications. As an added benefit, a robust quality control manufacturing screening test offers the ability to specify fracture toughness, which is a basic material property, as a purchasing requirement. The manufacturing screening fracture toughness test can also be incorporated into statistical process control on a manufacturing factory floor to reduce cost, improve quality, and to evaluate independently the success of the inspection and nondestructive evaluations. In addition, the manufacturing screening fracture toughness test can be used to research how changes in materials processing control fracture toughness so as to provide testing feedback between various manufacturing processes and mechanical behavior of the ceramics.

There are basically two different classes of tests for fracture toughness of brittle materials such as ceramics. The first class is a direct measurement in which the applied stress state at which a crack grows is measured. The second class is based upon indentation techniques and is indirect because the applied stress state is inferred from semiquantitative estimates of residual stress based upon an indirect dimensional argument. In the direct measurement, a starting crack or flaw of known size and shape is placed in the test specimen. The geometry of the starting crack directly gives the stress concentration of the crack based upon either an analytical solution or a finite element solution. The specimen is then loaded so that the crack is under tension. Both the observed applied load at which the crack grows and the calculated stress concentration of the crack are combined to give directly the ceramic fracture toughness of the ceramic. For a standard direct test of fracture toughness, the fracture toughness is defined by the observed load at which the crack grows and the geometry of the starter crack, which provides the stress concentration at the starter crack.

Examples of direct measurements include the chevron notch, bridge indentation, double cantilever beam and Tattersall-Tappin tests. Unfortunately, these tests all use a rectilinear or cylindrical specimen that typically has a largest linear dimension that is on the order of several centimeters. In contrast, ceramic balls used in even the largest capacity hybrid bearings have a diameter of much less than 1.5 cm, which makes it virtually impossible to fabricate specimens for any of these standard fracture tests due to the spherical shape of the balls and the limited volume of the balls.

As an alternative, the indentation test is currently used in industry to measure the fracture toughness of the ceramic balls. In this test, either a Vickers or Knoop indenter is used to make a pyramidal indentation in the surface of the ceramic. Indentation tests are indirect and semiquantitative. At a sufficiently high applied indentation load, cracks can grow from the corners of the indentation as the indentation is loaded. The length of the produced cracks and the maximum applied load are used to calculate the fracture toughness of the ceramic. In contrast to the direct tests, crack growth is not caused directly by the applied load but is instead caused physically by accommodation of displaced material aft r the crack is unloaded. The indentation test is, however, not rigorously quantitative. The calculation is based upon an estimate of the residual tensile stresses caused by the indentation. The estimate is not based upon direct measurements but is instead based upon a simple and crude dimensional analysis. The calculation also requires a constant that characterizes the volumetric change during indentation due to plastic flow of the indented ceramic. A value for the constant is selected that only averages the observed volumetric change of all the different ceramics ever measured. Ideally, the constant should be calibrated through an independent measurement of the toughness of the ceramic.

Disadvantageously, there is no current known test that can independently measure the fracture toughness of the ceramic balls. The existing fracture toughness test methods are disadvantageously indirect and imprecise because these test methods rely upon a semiquantitative estimate of residual stress. In addition, these have an additional source of imprecision because the residual stress estimate should ideally be calibrated through an independent direct measurement of fracture toughness. Disadvantageously, the existing test methods that directly measure the fracture toughness have only been applied to rectilinear specimens. These and other disadvantages are solved or reduced using the invention.

SUMMARY OF THE INVENTION

An object of the invention is to provide fracture toughness measurement method for brittle balls.

Another object of the invention is to provide fracture toughness direct measurement method for brittle balls.

Yet another object of the invention is to provide fracture toughness direct measurement method for brittle balls using applied compressive loads to produce tensile stress.

Still another object of the invention is to provide fracture toughness direct measurement method for brittle balls using applied compressive loads to produce tensile stress while directly observing indentation crack growth.

A further object of the invention is to provide fracture toughness direct measurement method for brittle balls using compressive conforming north-south opposing arc loads while directly observing equatorial indentation crack growth.

The present invention is directed to a mechanical test method for directly measuring the fracture toughness of brittle balls such as ceramic and steel ball bearings. For example, the mechanical test method can be used to directly measure the fracture toughness of the silicon-nitride balls used in hybrid bearings. Using this test method, a starter crack is first placed in the ball at an equatorial position on the surface of the ball. The ball is then placed between opposing platens that have hemispherical sockets with radii equal and conforming to the radius of the spherical ball under test. Importantly, the depth of the hemispherical sockets is less than the radius of the ball, such that the sockets are not a complete hemisphere and such that the angular arc length of the socket from the mating north and south poles of the sockets is less than ninety degrees. Consequently, the middle span of the ball, particularly about the equator of the ball, is not in contact with the hemispherical shaped sockets.

The starter crack is first positioned at the middle span of the ball along the equator of the ball. Preferably, two opposing platens are pushed towards each other under an applied load along the vertical axis through the respective opposing north and south poles of the two opposing platens. Under the applied load, as the inner socket surfaces apply compression forces upon the ball under test along the conforming angular arc length, the middle span of the ball at the equator slightly bulges outwardly. This equatorial bulging causes a tensile stress in the angular or hoop direction at the middle span along the equator of the brittle ball under test. Under a sufficiently high applied load, a tensile hoop stress develops at the middle span that is intense enough to cause the starter crack to grow in length. The crack growth is preferably directly observed by optical imaging using, for example, an optical microscope. As part of the direct test method of fracture toughness, the fracture toughness is defined by the observed load at which the crack grows and the geometry of the final crack, which naturally provides a stress concentration for the crack. The test method directly provides a measurement of the fracture toughness of the ball under test. The test method is specialized for the spherical brittle balls that may have small spherical volumes. These and other advantages will become more apparent from the following detailed description of the preferred embodiment.

DETAILED DESCRIPTION OF THE PREFERRED EMBODIMENT

Figure 1:
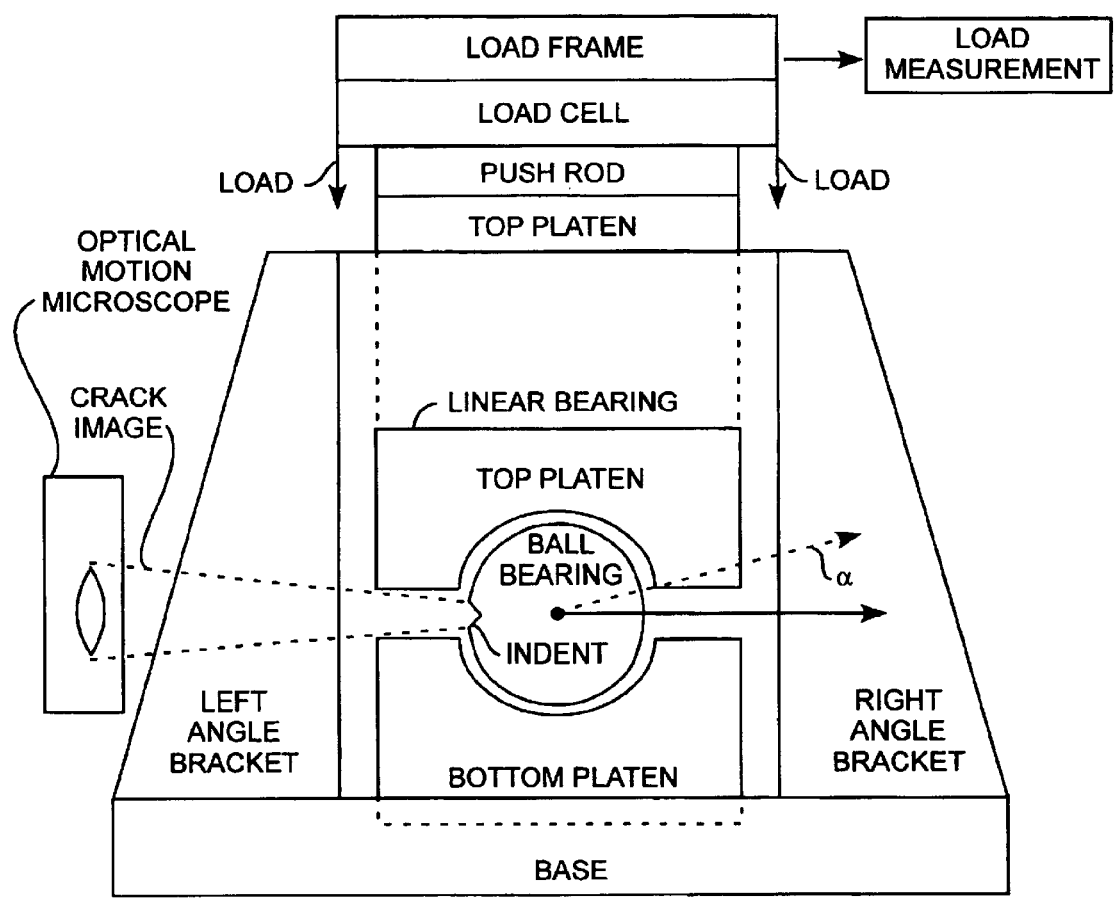
FIG. 1 is a diagram of a fracture toughness test fixture.

An embodiment of the invention is described with reference to the figures using reference designations as shown in the figures. Referring to FIG. 1, the mechanical test method can be implemented using a fracture toughness text fixture for directly measuring the fracture toughness of ceramic balls, such as are used in modern hybrid bearings. In practicing the method, a starter crack is first placed in the ball prior to the ball being placed in the test fixture. The ball is placed between opposing platens that have hemispherical sockets with radii equal to the radius of the ball radius. However, the depth of the hemispherical sockets is less than the radius of the ball. That is, the sockets of the lateens have a radial arc length that is less than a complete hemisphere such that the conforming arc length is less than ninety degrees from the north pole for the top platen and equally less than ninety degrees for the south pole, so that the midspan or equator of the ball does not contact the incompletely conforming hemispherical sockets because the depth of the sockets is less than the radius of the ball. The depth of the sockets is defined by the conforming angle α. Hence, the incompletely conforming hemisphere sockets are defined by the conforming angle α that is less than ninety degree from the poles, and, in the preferred form, is 75°±10 degree. The nominal 75° off the poles of the platens is an optimum conforming angle α that is also nominally 15° off the equator of the ball.

To run the test, the two platens are compressed along the vertical axis extending through the north and south poles of the two platens as well as the ball under test. Using this vertically aligned pole orientation, the ball is compressed by the platens at the north pole and south pole. The middle span at the equator of the ball is not in contact with the incompletely conforming hemispherical sockets. A load cell is used for providing a measurement of the applied load. The load frame uses a push rod to apply the load to the top platen being pushed under the applied load towards the bottom platen supporting the ball under test. The top platen is supported by and moves through a linear bearing. The load frame may be an adapted Instron load frame. The ball rests in the conforming socket of the bottom platen. The linear bearing is disposed between left and right frame brackets coupled and supported by a base in which is disposed the bottom platen. Under a nominal applied load, the push rod pushes the top platen through the linear bearing towards the bottom platen until the conforming socket of the top platen makes contact with the ball under test with the north poles and south poles of the top and bottom sockets aligned with the north and south poles of the ball under test. At the time of contact, the applied load increases so as to apply a compressive force upon the ball across the conforming sockets. The middle equator of the ball begins to bulge outwardly as the applied load is increased, causing a tensile stress in a hoop direction at the equator. The starter precrack begins to grow under the tensile stress. The starter precrack can be as great 1.33 mm. An imaging device, such as an optical motion microscope, can be used to image the crack growth while the ball is under the applied load, such that the text fixture can provide measurements of crack growth under the applied load, from which the fracture toughness can be automatically computed by a computer that receives the crack growth data from the microscope and applied load data from the load cell. The microscope can be adapted to include or couple to a computer processor receiving applied load data from the load cell while further receiving crack growth data from the microscope.

Figure 2:
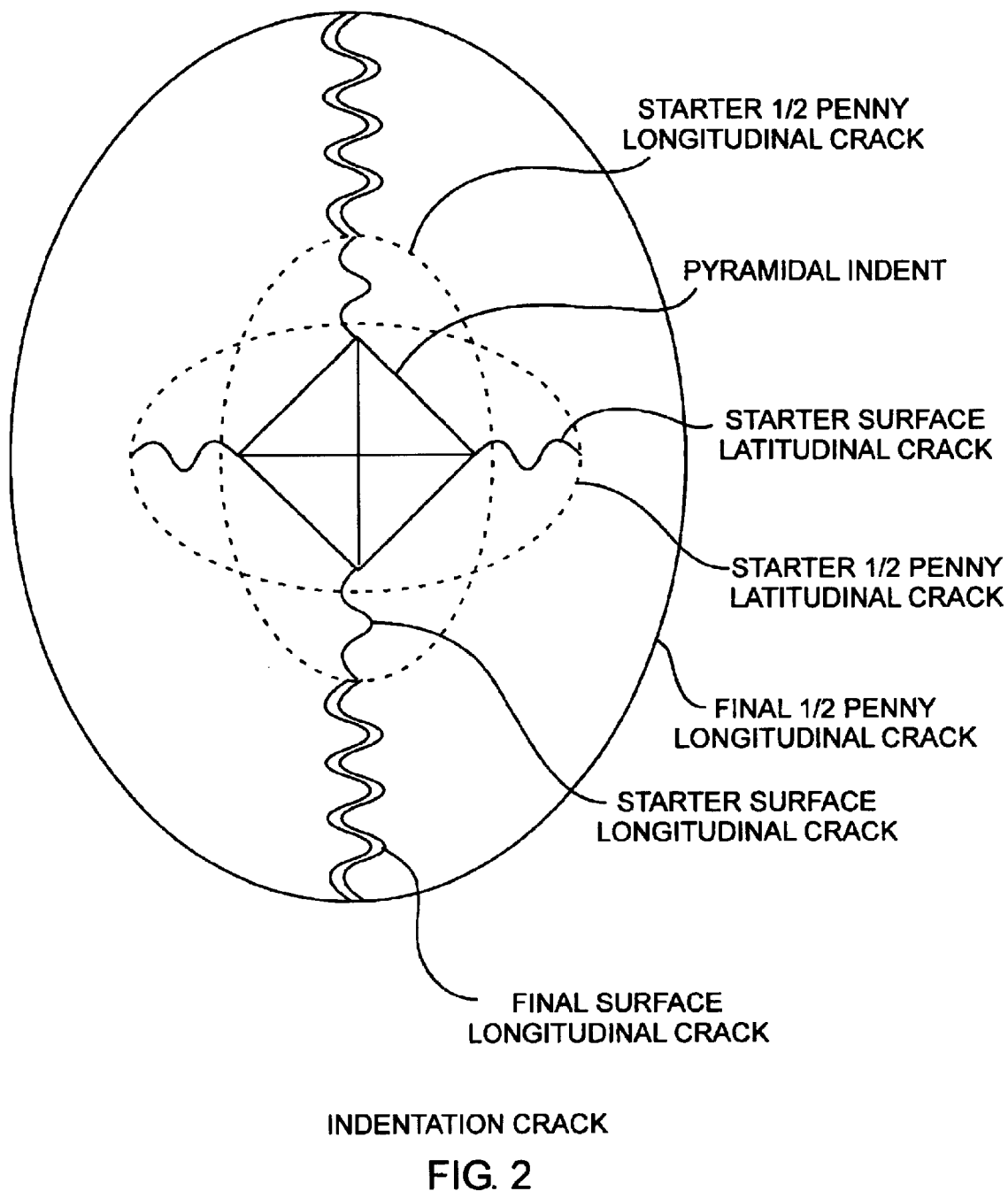
FIG. 2 is a diagram of an indentation crack.

Referring to FIGS. 1 and 2, and more particularly to FIG. 2, an indentation is placed in the ball. Conventional indentations methods can be used that employ a hard diamond tool having a pyramidal point that is struck into the surface of the ball. When struck, a starter surface latitudinal crack is disposed in a half penny latitudinal crack and a starter surface longitudinal crack is disposed in a half penny longitudinal crack. Under the applied stress, the starter surface longitudinal crack grows to a final surface longitudinal crack. Longitudinal crack growth is imaged and measured by the crack motion microscope as a function of the applied load measured by the load cell. The microscope can image the radial distance from the center of the pyramidal indent to the further extent of the surface crack so as to measure the time rate of change of crack growth relative to an applied load.

Figure 3:
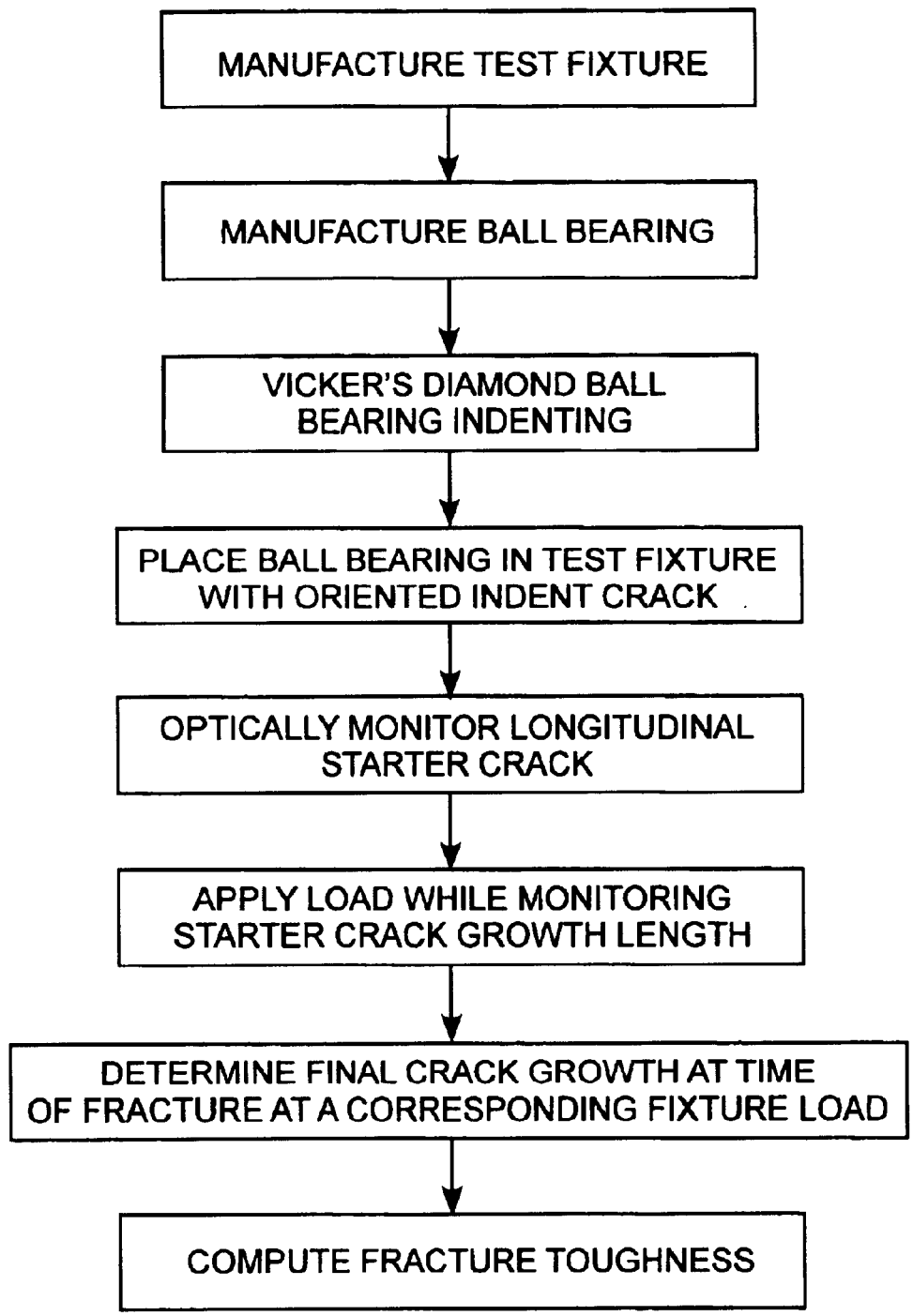
FIG. 3 is a flow diagram of a fracture toughness test method.

Referring to FIGS. 1, 2, and 3, and more particularly FIG. 3, the test method is preferably implemented using a manufactured text fixture, such as the preferred fracture toughness test fixture shown in FIG. 1. A brittle ball is manufactured. The brittle ball can be made of various materials, such as from ceramics and steel. Destructive starter precracks are struck into the ball. The precracks are preferably created on the surface of the ball when struck by a conventional Vickers diamond tool having a pyramidal point for creating the indentation in the ball under test. When striking the ball, the longitudinal and latitudinal surface starter cracks are formed. Hence, the placement of the indentation on the surface of the ball defines the north and south poles aligned to two opposing vertical corners of the indentation that point longitudinally toward the north and south poles, and defines the horizontal equator of the ball aligned with two opposing horizontal corners of the indentation, such that, the two longitudinal starter precracks are aligned towards the poles and the two latitudinal starter precracks are aligned with the equator. As such, the indentation defines the desired placement of the ball in the bottom platen of the text fixture. Imaging the indentation as well as the longitudinal starter precracks with respect to alignment in the bottom platen can then optically image the ball to determine that the ball has been accurately disposed in the bottom platen. That is, the ball is positioned in the bottom platen with the starter precrack placed at the equator with the axis of the longitudinal precracks perpendicular to the equator. The longitudinal precrack points toward the north and south poles while centered on the equator of the ball, which rests in the conforming socket of the bottom platen. The load frame applies an initial low push load to the push rod to push the top platen towards the ball until the conforming socket of the top platen makes conforming mating contact with the north hemispherical surface of the ball under test. The load frame then applies an increasing amount of load upon the top platen to apply an increasing amount of load upon the ball. Under a sufficiently high applied load, a tensile hoop stress develops at the equator that is intense enough to cause the precracks to grow. The crack growth is observed directly by the optical microscope. In situ images of the ball under test are captured while the ball is under load. Using conventional computational practices, the fracture toughness is defined by the observed load at which the crack grows and the geometry of the precracks, which defines the stress concentration. The fracture toughness is directly computed from the crack growth, the geometry of the precracks, and the applied load. The test method is specialized for the spherical balls that may have small spherical volumes.

Figure 4A:
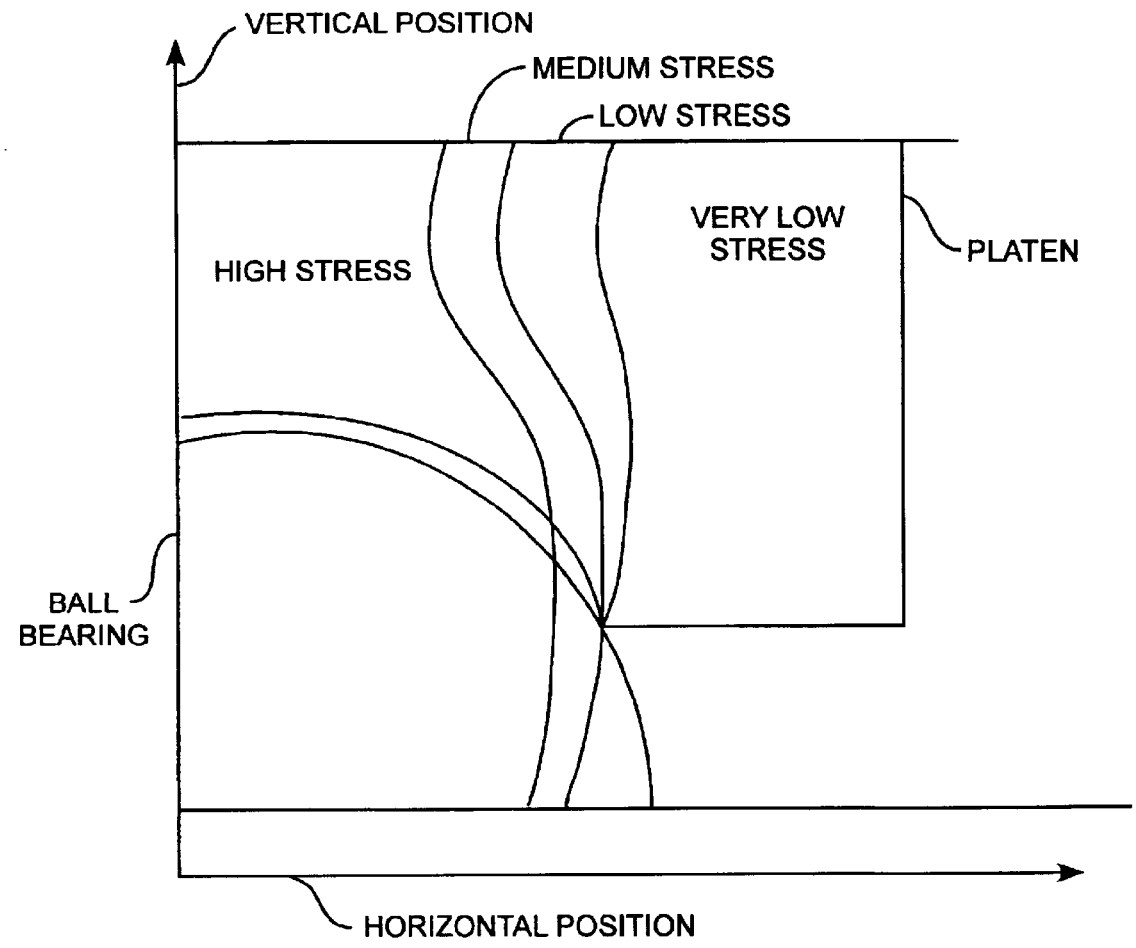
FIG. 4A is a compressive stress contour plot of a brittle ball under test.
Figure 4B:
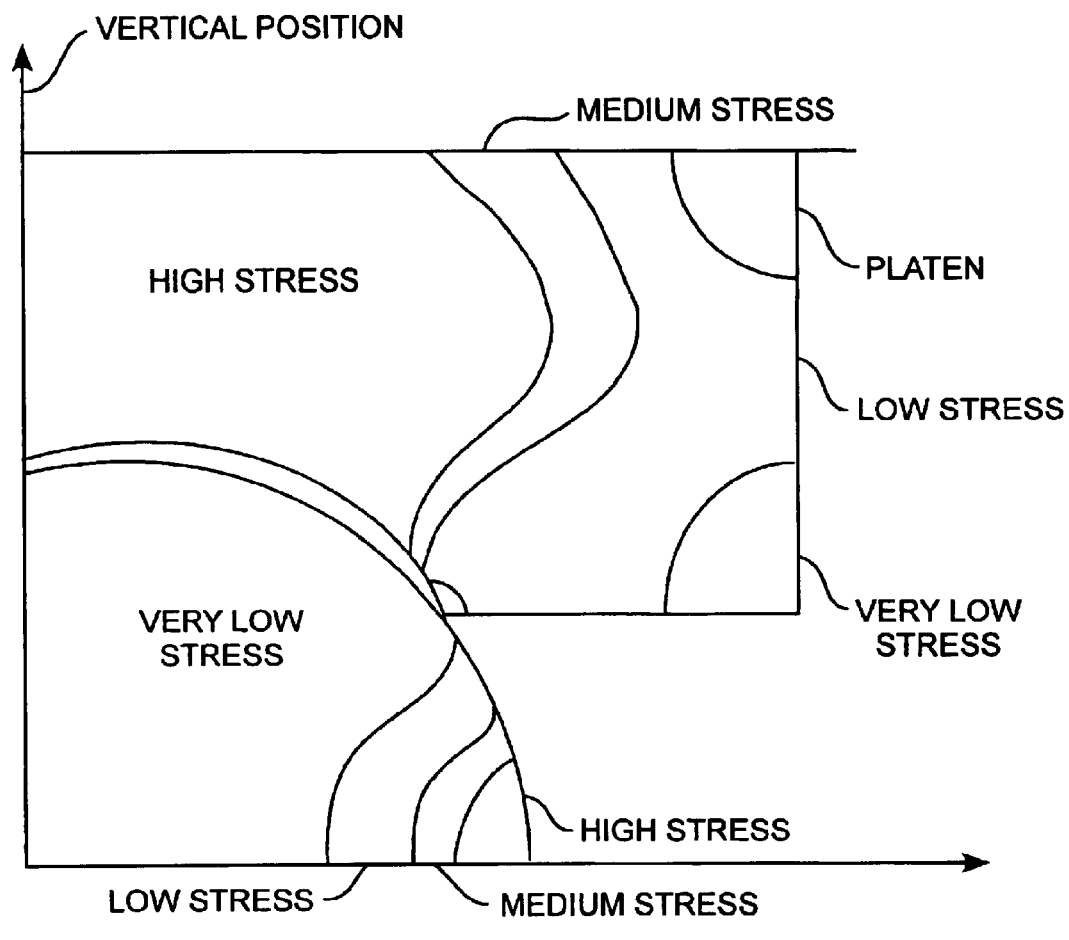
FIG. 4B is a tensile stress contour plot of a brittle ball under test.

Referring to FIGS. 1, 2, 3, 4A and 4B, and particularly FIGS. 4A and 4B, compressive stresses and tensile stresses are created in the ball under test, as well the top platen. Of particular interest is the hoop tensile stress that develops at the equator when the ball is compressed at the two poles. The tensile stress can be calculated using finite element analysis. An axisymmtric calculation can be performed to show the compressive and tensile stresses in a slice through the ball under test. The gradation from high, medium, low, and very low compressive stress and tensile stress extends through the ball and platen. The tensile stresses are highest at the equator. The compressive applied load is effectively translated into hoop tensile stress at the equator of the ball under test.

Figure 5:
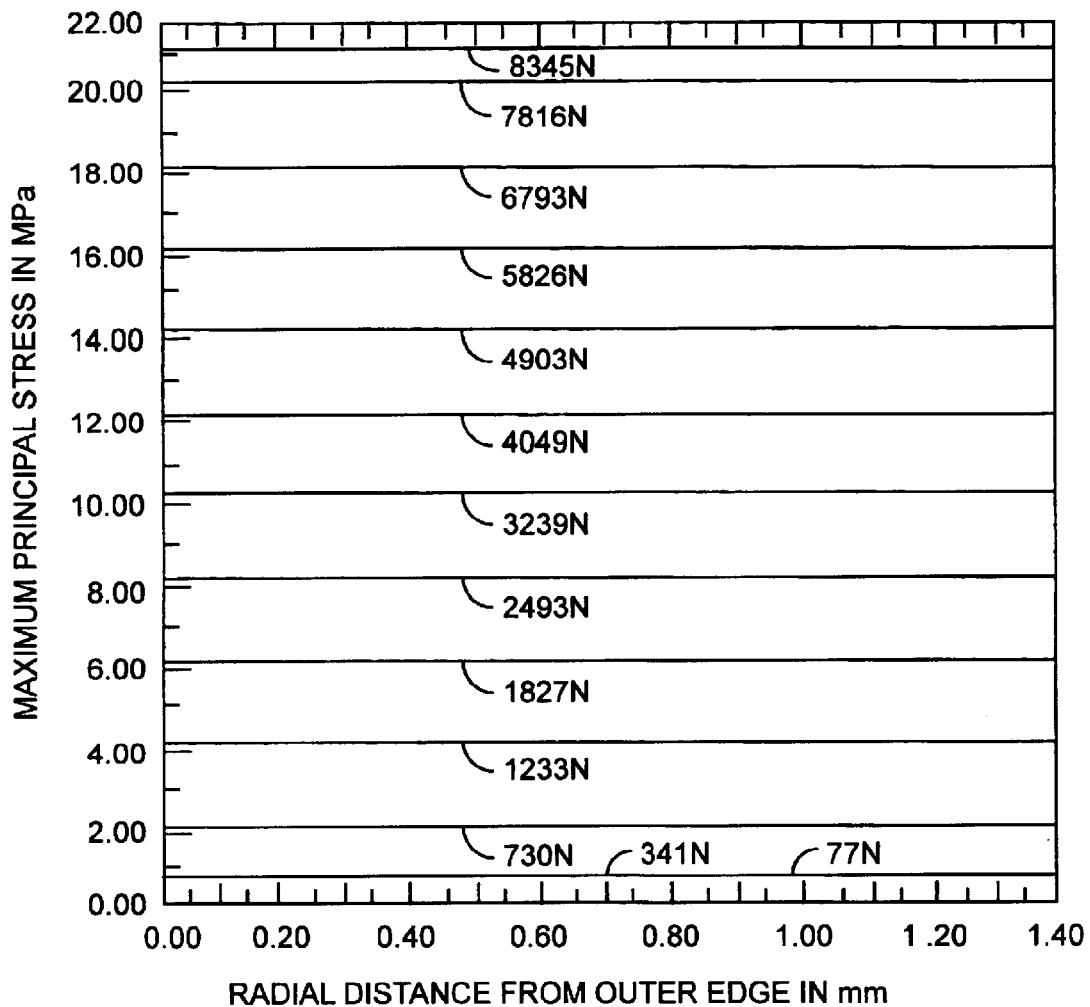
FIG. 5 is a crack length to tensile stress graph for various applied loads.

Referring to all of the Figures, and particularly to FIG. 5, isocontours are shown for maximum principal stresses in MPa as a function of the radial position at the equator for different applied loads in Newtons N. As shown, the isocontours are relatively flat across radial position. The longitudinal precrack grows in the north and south directions from the top and bottom edges of the longitudinal precracks. The north and south directions are orthogonal to the applied tensile hoop stresses at the equator. Therefore, the north to south direction is the preferred direction for crack growth. The starter precrack is modeled as a half penny crack. The half penny cracks are characterized by two dimensions including the length 2C of the crack at the surface and the depth A of the crack. The stress intensity factor K for the half penny crack is a function of the ratio A/C and the square root of depth A and is given by the K fracture toughness equation, $K=[1.13-0.09(A/C)]\sqrt{[\pi/Q^{o\sqrt{A}}]}$. In the fracture toughness equation, $Q=1+1.464(A/C)^{1.65}$, the term σ is the applied tensile stress field, K is the fracture toughness, Q is a geometric factor, C is the half penny crack radius on the surface, and A is the half penny crack radius into the depth of the material. The ratio A/C is one when the half penny crack is a perfect half circle. Mathematically, K has two terms that are proportional to the depth A and one term that is inversely proportional to A. For this reason, K is not a strong function of the depth A because the proportional and inversely proportional terms counterbalance. Hence, the starting half penny precrack can tolerate errors in characterizing depth A for a given value of the length C. Therefore, the fracture toughness K depends more strongly on σ than on the depth A, for a given value of length C. Hence, the computation accurately provides the fracture toughness K when the length C can be measured accurately, even when the depth A can not be accurately measured.

For example, the applied stress field can be calculated by finite element analysis. The stress field at the equator for different loads applied of the fixture can be determined for balls of differing materials. Along the x-axis of the isocontours, a radial distance of 0.0 mm corresponds to the outer diameter of the ball. An increasing radial distance represents an increasing depth into the ball from the surface. Hence, a half penny crack that is 0.5 mm deep, where A=0.5 mm, is at a radial distance of 0.5 mm. The y-axis of the isocontours provides the maximum principal stress as a function of load applied into the test fixture. The maximum principal stress is tensile and is the stress component responsible for fracture during the test. To calculate the fracture toughness K from the fracture toughness equation, the maximum principal stress is used as the applied tensile stress field σ.

Images of a ball are obtained for crack growth at an applied load, for example, of 6003 N, with the starter precrack positioned at the equator of the ball between the platens and under a load of 5000 N before crack growth occurred. Successful formation of crack growth from the starter precrack may occur at an exemplar applied load of 6003 N. Imaging magnifications may be at 100× for crack growth recognition. Florescent backlighting may be used for highlighting the precrack and crack growth. An image of the surface of the precrack can provide a value for length C, but depth A is not directly known. However, it is commonly known that a Vickers indentation provides a circular precrack for which A/C=1. For example, with a crack length of 2C=1.56 mm, A=0.778 mm by direct inference. For such an exemplar precrack, the crack is imaged to grow at an applied load of 6003 N. From the isocontours, an applied load of 6003 N provides a maximum principal stress of σ=16.0 MPa at A=0.778 mm by interpolating between applied load isocontours. From the fracture toughness equation, the fracture toughness is computed to be K=0.52 MPa√m which compares to the handbook values for glass, for example.

To test the sensitivity of the calculation to errors in the value of A/C, with A/C=0.5, and A=0.39 mm, using a Vickers indentation. The applied load isocontours are very flat over the typical range of A for the xperimentally measured applied loads. Hence, the value of σ is unchanged at a value of 16 MPa. From fracture toughness equation, K=0.50 MPa√m. Remarkably, the calculated fracture toughness is relatively immune to errors in characterizing the ratio A/C. In addition, because the applied load isocontours are very flat, the value of a used in fracture toughness equation is also relatively immune to errors in characterizing both the depth A and the ratio A/C. Hence, the proposed mechanical test method is immune to errors in measuring A and A/C because the maximum principal stress is uniform over the relevant size scale of the typical precrack because of the uniform isostress contours. Hence, the test is also equally immune to errors in positioning the precrack at the equator even when the errors in positioning the ball in the bottom platen are of the order of the length scale of the precrack. The uniformity of the applied tensile stress field makes the test robust and offers repeatable manufacturing precision.

The invention is directed to a test method that directly images crack growth at an applied load for directly computing the fracture toughness of brittle balls. The method is precise, rigorous, immune to errors, and is fully quantitative. The ball under test is compressed along the north and south poles of the ball, which causes the equatorial bulging under high tensile stresses where crack growth occurs at a sufficiently high applied load. Ball is precracked preferably by a diamond indenter. The longitudinal precracks cr at d by the indentation are placed at equator and point vertically towards the north and south poles of the ball. The ball is compressed by conforming north and south opposing hemispherical platen sockets generating hoop tensile stress s at equator where the longitudinal crack growth occurs at the sufficiently high applied load. The fracture toughness is directly computed from imaging of the crack length and known values of the applied stress for the critical load at which the crack grows unstably. The conforming mating hemispherical platens are incompletely conforming, that is less than 90° in arc length angle from the poles. Too low an angle and the ball is crushed at the poles. At too high an angle, the equator does not bulge to give required tensile hoop stress. Finite element analysis shows that an arc length angle α of 75°±10° is preferred. The test method measures the fracture toughness of a wide variety of brittle material balls including ceramics and steel ball bearings, such as 52100 steel bearing class balls with fracture toughnesses K up to 15.0 MPa√m with precracks preferably having a length 2C of greater than 1.3 mm. The test method enables direct measurement of the fracture toughness of ball bearings, such as silicon-nitride balls used in hybrid bearings. The method can be used by ball bearing manufacturers for screening lots of balls for fracture toughness requirements. The test can be applied using variously sized indenters and balls of differing materials and sizes. Those skilled in the art can make enhancements, improvements, and modifications to the invention, and these enhancements, improvements, and modifications may nonetheless fall within the spirit and scope of the following claims.

What is claimed is:

1. A method for determining the fracture toughness of a ball having an indentation defining an equator of the ball, the equator defining north and south poles of the ball, the indentation having precracks and a precrack length, the method comprising the steps of, applying an applied load in compression through opposing hemispherical surfaces having an arc length angle of less than ninety degrees, the opposing hemispherical surfaces conforming to the surfaces of the ball respectively at the north and south poles so that the ball bulges outwardly at the equator producing tensile stresses, load determining a critical applied load when the precrack begins to grow under the tensile stresses at the equator, and toughness determining the fractured toughness of the ball from the precrack length and the critical applied load.

2. The method of claim 1 wherein, the fracture toughness is less than 15.0 MPa√m.

3. The method of claim 1 wherein, the arc length angle is 75°±10°.

4. The method of claim 1 wherein, the precrack length is less than 1.33 mm.

5. The method of claim 1 wherein, the ball is made of silicon nitride.

6. The method of claim 1 wherein, the ball is a made of a ceramic material.

7. The method of claim 1 wherein, the ball is made of steel.

8. The method of claim 1 wherein, the indentation is a pyramidal indent providing a half penny crack defining the precrack.

9. The method of claim 1 wherein, the indentation is a Vickers indent providing a half penny crack defining the precrack.

10. The method of claim 1 wherein, the toughness determining step comprises the step of computing the toughness from a fracture toughness equation $K=[1.13-0.09(A/C)]\sqrt{[\pi/Q^{\sigma\sqrt{A}}]}$, wherein Q is a geometric factor of the indent such that $Q=1+1.464(A/C)^{1.65}$, σ is an applied stress field created in the ball under the applied load, K is the fracture toughness, C is a half penny crack radius of the precrack on the surface of the ball, and A is a half penny crack radius into the depth of the material, where the ratio A/C is equal to one when the half penny crack is a perfect half circle.

11. The method of claim 10 wherein, the applied stress field is a maximum principal stress in MPa and is predetermined from the size and material of the ball.

12. The method of claim 1 wherein, the precrack comprises two longitudinal precracks respectively extending from opposing north and south corners of the indent towards the north and south poles of the ball.

13. The method of claim 1 wherein, the applied load is applied through a load frame applying the applied load to a top platen having a top conforming socket defining a top hemispherical surface of the opposing hemispherical surfaces, and the ball is disposed in a bottom platen having a bottom conforming socket defining a bottom hemispherical surface of the opposing hemispherical surfaces.

14. The method of claim 1 wherein the load determining step comprising, imaging the precracks prior to the applying step, imaging the precracks during the applying step, and imaging the precracks when the precrack begins to grow when the applied load is at the critical applied load.

15. The method of claim 14 wherein the imaging steps using an imaging microscope focused upon the precrack position at the equator of the ball during the applying step.

16. The method of claim 1 wherein, the precrack comprises opposing half penny latitudinal precracks and opposing half penny longitudinal precracks.

* * * * *